(12) United States Patent
Escher et al.

(10) Patent No.: US 8,778,327 B2
(45) Date of Patent: Jul. 15, 2014

(54) SUBSTANCES, COMPOSITIONS AND METHODS FOR PREVENTING AND TREATING IMMUNE-MEDIATED INFLAMMATORY DISORDERS

(75) Inventors: Alan P. Escher, Redlands, CA (US); Fengchun Li, Loma Linda, CA (US)

(73) Assignee: Loma Linda University, Loma Linda, CA (US)

( * ) Notice: Subject to any disclaimer, the term of this patent is extended or adjusted under 35 U.S.C. 154(b) by 132 days.

(21) Appl. No.: 11/913,657

(22) PCT Filed: May 5, 2006

(86) PCT No.: PCT/US2006/017763
§ 371 (c)(1),
(2), (4) Date: Nov. 5, 2007

(87) PCT Pub. No.: WO2006/124375
PCT Pub. Date: Nov. 23, 2006

(65) Prior Publication Data
US 2008/0194510 A1 Aug. 14, 2008

Related U.S. Application Data

(60) Provisional application No. 60/680,249, filed on May 11, 2005.

(51) Int. Cl.
*A01N 63/00* (2006.01)
*C12N 5/00* (2006.01)

(52) U.S. Cl.
USPC .......................................... 424/93.1; 435/325

(58) Field of Classification Search
USPC .......................................... 424/93.1; 435/325
See application file for complete search history.

(56) References Cited

U.S. PATENT DOCUMENTS

| | | | |
|---|---|---|---|
| 6,410,273 | B1 | 6/2002 | Crouzet et al. |
| 2003/0176378 | A1 | 9/2003 | Weiner et al. |
| 2006/0153842 | A1 | 7/2006 | Lake et al. |
| 2010/0068813 | A1 | 3/2010 | Li et al. |
| 2012/0308577 | A1 | 12/2012 | Li et al. |

FOREIGN PATENT DOCUMENTS

| | | |
|---|---|---|
| WO | WO-99/44644 A1 | 9/1999 |
| WO | WO-99/44644 A1 | 9/2000 |
| WO | WO 00/59538 A | 10/2000 |
| WO | WO-00/59538 A2 | 10/2000 |
| WO | 2004/034966 A2 | 4/2004 |
| WO | WO-2004/034966 A2 | 4/2004 |

OTHER PUBLICATIONS

Guenette et al., DNA methylation inhibits transcription of procollagen alpha 2(I) promoters, Biochem J. 283 ( Pt 3):699-703, 1992.*
Szabó et al., Structure and the promoter region of the mouse gene encoding the 67-kD form of glutamic acid decarboxylase, DNA Cell Biol. 15(12):1081-91, 1996.*
Igate et al., Molecular cloning and functional analysis of the murine bax gene promoter, Gene 238(2):407-15, 1999.*
Nakao et al., Regulation of transcription and chromatin by methyl-CpG binding protein MBD1, Brain Dev. 23 Suppl 1:S174-6, 2001.*
Zardo et al., Dynamic and reversibility of heterochromatic gene silencing in human disease, Cell Research 15(9):679-90, 2005.*
Borner, Christoph et al., J. Cell Biol., Aug. 1994, vol. 126, No. 4, pp. 1059-1068.
Contreras Juan L. et al., "Cytoprotection of pancreatic islets before and early after transplantation using gene therapy," Kidney International, Jan. 2002, vol. 61, No. 1, Suppl., pp. 79-84.
Contreras Juan L. et al., "Gene transfer of the Bcl-2 gene confers cytoprotection to isolated adult porcine pancreatic islets exposed to xenoreactive antibodies and complement," Surgery, Aug. 2001, vol. 130, No. 2, pp. 166-174.
Efrat S. et al., "Adenovirus Early Region 3 (E3) Immunomodulatory Genes Decrease the Incidence of Autoimmune Diabetes in NOD Mice," Diabetes, May 2001, vol. 50, No. 5, pp. 980-984.
Filippova, M. et al., "Effects of Plasmid DNA Injection on Cyclophosphamide-Accelerated Diabetes in NOD Mice," DNA and Cell Biology, Mar. 2001, vol. 20, No. 3, pp. 175-181.
Ilan, Y. et al., "Insertion of the adenoviral E3 region into a recombinant viral vector prevents antiviral humoral and cellular immune responses and permits long-term gene expression," Mar. 1997, Proc. Natl. Acad. Sci. USA, vol. 94, pp. 2587-2592.
Kagawa, S. et al., "A binary adenoviral vector system for expressing high levels of the proapoptotic gene bax," Gene Therapy (2000), 7, pp. 75-79.
Klinman, D. et al., "Use of CpG oligodeoxynucleotides as immune adjuvants," Imm. Rev., 2004, vol. 199, pp. 201-216.
Li, Alice et al., "Co-delivery of pro-apoptotic BAX with a DNA vaccine recruits dendritic cells and promotes efficacy of autoimmune diabetes prevention in mice," Vaccine 22 (2004) pp. 1751-1763.
Li, Alice et al., "Pro-apoptotic DNA vaccination ameliorates new onset of autoimmune diabetes in NOD mice and induces foxp3+ regulatory T cells in vitro," Vaccine 24 (2006) pp. 5036-5046.
Krieg, Arthur M., "The role of CpG motifs in innate immunity," Curr. Opin. Immun., 2000, vol. 12, pp. 35-43.
Mathisen et al., "Gene Therapy in Experimental Autoimmune Encephalomyelitis," (2000) J. Clin. Immunol., vol. 20 (5), pp. 327-333.

(Continued)

*Primary Examiner* — Anoop Singh
*Assistant Examiner* — David A Montanari
(74) *Attorney, Agent, or Firm* — James W. Hill; McDermott Will & Emery LLP

(57) ABSTRACT

A substance or a composition for preventing, delaying the onset of or treating one or more than one immune-mediated inflammatory disorder in an organism who is susceptible to developing the immune-mediated inflammatory disorder, who is developing the immune-mediated inflammatory disorder or who has the immune-mediated inflammatory disorder. A method of preventing, delaying the onset of or treating an organism who is susceptible to developing the immune-mediated inflammatory disorder, who is developing the immune-mediated inflammatory disorder or who has the immune-mediated inflammatory disorder.

11 Claims, 10 Drawing Sheets

(56) References Cited

OTHER PUBLICATIONS

Pierce, M. A. et al., "Adenovirus Early Region 3 Antiapoptotic 10.4K, 14.5K, and 14.7K Genes Decrease the Incidence of Autoimmune Diabetes in NOD Mice," Diabetes, vol. 52, May 2003, pp. 1119-1127.

Rabinovitch A. et al., "Transfection of Human Pancreatic Islets With an Anti-Apoptotic Gene (bcl-2) Protects B-Cells From Cytokine-Induced Destruction," Diabetes, Jun. 1999, vol. 48, No. 6, pp. 1223-1229.

Scheule, R. K., "The role of CpG motifs in immunostimulation and gene therapy," Adv. Drug Delivery Rev., 2000, vol. 44, pp. 119-134.

Simone, E. A. et al., "Immunologic 'Vaccination' for the Prevention of Autoimmune Diabetes (Type 1A)," Diabetes Care, vol. 22, Suppl. 2, Mar. 1999, pp. B7-B15.

Tokui M. et al., "Studies on prevention of diabetes in NOD mice by Intramuscular administration of plasmid expressing GAD and IL-4," Chemical Abstracts + Indexes, American Chemical Society, Columbus, OH, US, vol. 25, No. 125, 1996, p. 1148.

Trucco, M. et al., "Gene Therapy Strategies to Prevent Autoimmune Disorders," Current Gene Therapy, 2002, vol. 2, pp. 341-354.

European Search Report issued Jun. 16, 2005 in related European Patent Application No. 03808948.8.

International Search Report and Written Opinion issued in parent International Patent Application No. PCT/US2006/17763 on Sep. 20, 2007.

Hu, Y., et al., Chapter 6, "Cell Apoptosis and message Transduction," see "Molecular Medicine of Apoptosis," Military Medical Science Press, Beijing, first edition, pp. 93-101. (no translation is available).

Schowalter, D.B. et al., "Heterologous Expression of Adenovirus E3-gp19K in an E1a-Deleted Adenovirus Vector Inhibits MHC I Expression in Vitro, But Does Not Prolong Transgene Expression in Vivo," Gene Therapy (1997) 4, pp. 351-360.

Balasa, B. et al., "Vaccination with glutamic acid decarboxylase plasmid DNA protects mice from spontaneous autoimmune diabetes and B7/CD28 costimulation circumvents that protection," Clin. Immunol., 2001, vol. 99, No. 2, pp. 241-252.

Chao, D. T. et al., BCL-2 family : regulators of cell death, Annu. Rev. Immunol., 1998, vol. 16, pp. 395-419.

Chattergoon, M. A., et al., "Targeted antigen delivery to antigen-presenting cells including dendritic cells by engineered Fas-mediated apoptosis," Nat. Biotechnol., 2000, vol. 18, No. 9, pp. 974-979.

Chernysheva, A. D., el al., "T cell proliferation induced by autologous non-T cells is a response to apoptotic cells processed by dendritic cells," J. Immunol., 2002, vol. 169, No. 3, pp. 1241-1250.

Restifo, N. P., "Building better vaccines: how apoptotic cell death can induce inflammation and activate innate and adaptive immunity," Curr. Opin. Immunol., 2000, vol. 12, No. 5, pp. 597-603.

Sasaki, S. et al., "Apoptosis-mediated enhancement of DNA-raised immune responses by mutant caspases," Nat. Biotechnol., 2001, vol. 19, No. 6, pp. 543-547.

Tisch, R. et al., "Antigen-specific mediated suppression of beta cell autoimmunity by plasmid DNA vaccination," J. Immunol., 2001, vol. 166, No. 3, pp. 2122-2132.

Pasquini et al., "The Effect of CpG Sequences on the B Cell Response to a Viral Glycoprotein Encoded by a Plasmid Vector," Gene Therapy, MacMillan Press Ltd., Basingstoke, GB, vol. 6, No. 8, Aug. 1, 1999, pp. 1448-1455.

European Search Report issued in corresponding European Patent Application No. 09000207.2 on Apr. 16, 2009.

Miranda et al., "DNA Methylation: The Nuts and Bolts of Repression,"J. Cell. Physiol. 213: 384-390, 2007.

Razin, "CpG Methylation, Chromatin Structure and Gene Silencing—a Three-Way Connection," The EMBO Journal, vol. 17, No. 17, pp. 4905-4908, 1998.

Komura, et al., "Repression of transient expression by DNA methylation in transcribed regions of reporter genes introduced into cultured human cells," Biochimica et Biophysica Acta, 1995, pp. 73-78, vol. 1260.

Qu, et al., "Demethylation and expression of methylated plasmid DNA stably transfected into HeLa cells," Nucleic Acids Research, 1999, pp. 2332-2338, vol. 27, No. 11.

Li, et al., "A therapeutic DNA vaccination strategy for autoimmunity and transplantation," Vaccine, 2010, pp. 1897-1904, vol. 28.

Guenette, D., et al., "DNA methylation inhibits transcription of procollagen α2(1) promoters," Biochem J. (1992) 283, 699-703.

Adamus, et al., "Autoimmunity against Carbonic Anhydrase II Affects Retinal Cell Functions in Autoimmune Retinopathy", J. Autoimmun. 32(2): 133-139, 2009.

Belakova, et al., "DNA vaccines: are they still just a powerful tool for the future?" Arch Immunol Ther Exp (Warsz) 55(6): 387-98, (2007).

Bros, et al., "A newly established murine immature dendritic cell line can be differentiated into a mature state, but exerts tolerogenic function upon maturation in the presence of gluccocorticoid", Blood, vol. 109, pp. 3820-3829; (2007).

Bumgardner, et al., "Unusual patterns of alloimmunity evoked by allogeneic liver parenchymal cells", Immunol Rev. 174: 260-79, (2000).

Erickson, et al., "Expression of carbonic anhydrase II (CA II) promoter-reporter fusion genes in multiple tissues of transenic mice does not replicate normal patterns of expression indicating complexity of CA II regulation in vivo", Biochem Genet. 33(11-12): 421-37, (1995).

Hedstrand, et al., "The Transcription Factors SOX9 and SOX10 are Vitiligo Autoantigens in Autoimmune Polyendocrine Syndrome Type I", The Journal of Biological chemistry, 276(38): 35390-35395(2001).

Horner, et al., "Skin tolerance: in search of the Holy Grail", European Society for Organ Transplantation 21: 101-112, 2008.

Hosoda, et al., "Detection of autoantibody against carbonic anhydrase II in various liver diseases by enzyme-linked immunosorbent assay using appropriate conditions", Clinica Chimica Acta 342: 71-81, 2004.

Huurman, et al., "Cellular Islet Autoimmunity Associates with Clinical Outcome of Islet Cell Transplantation", PLoS One 3(6): e2435, 2008.

Iwata, et al., Anti-Type V Collagen Humoral Immunity in Lung Transplant Primary Graft Dysfunction, J. Immunol. 181(8): 5738-5747, 2008.

Kerkar, et al., "Cytochrome P4502D6193-212: A New Immunodominant Epitope and Target of Virus/Self Cross-Reactivity in Liver Kidney Microsomal Autoantibody Type 1-Positive Liver Disease", J. Immunol. 170: 1481-1489 (2003).

Klinman, et al., "Contibution of CpG motifs to the immunogenicity of DNA vaccines", Journal of Immunology, vol. 158, pp. 3635-3639 (2007).

Li et al. "DNA vaccines for transplantation", Expert Opin, Biol. Ther. 10(6): 903-915, (2010).

Lim, et al., "Curring Edge: Direct Suppression of B Cells by CD4+CD25+ Regulatory T Cells", J/ Immunol 175: 4180-4183 (2005).

Li, et al., "Decreased insulitis and blood glucose leves after injection of GAD-transduced lymphocytes into NOD mice", Mol. Ther. 6(6): 701-9, (2002).

Martin, et al., "Cell to cell interaction in the immune system", Journal of Experimental Medicine, vol. 128, pp. 855-874 (1968).

McGowan, et al., "Characterization of the rat carbonic anhydrase II gene structure: sequence analysis of the 5' flanking region and 3' UTR", Gene 186(2): 181-8, (1997).

Meinck, et al., "Antibodies against glutamic acid decarboxylase: prevalence in neurological diseases", J. Neurol Neurosurg Psychiatry 71: 100-103, 2001.

Ono, et al., "Carbonic Anhydrase in the membrane of the endoplasmic reticulum of male rat liver", Proc. Natl. Acad. Sci. vol. 89, pp. 11721-11725, Dec. 1992.

Peters, et al., "The Mouse as a model for human biology: a resource guide for complex trait analysis", Nature Reviews, vol. 8, pp. 58-69, Jan. 2007.

Reindl, et al., "Antibodies Against the Myelin Oligodendrcyte Glycoprotein and the Myelin Basic Protein in Multiple Sclerosis and Other Neurological Diseases: A omparative Study", Brain 122: 2047-2056, (2001).

(56) References Cited

OTHER PUBLICATIONS

Reyes-Sandoval, et al., "CpG Methylation of a Plasmid Vector Results in Extended Transene Product Expression by Circumventing Induction of Immune Responses", Molecular Therapy 9(2): 249-261 (2004).
Seetharam, et al., "Alloimmunity and Autoimmunity in Chronic Rejection", Curr Opin Organ Transplant 15(4): 531-536, (2010).
Steinman, et al., "The Induction of Tolerance by Dendritic Cells That Have Captured Apoptotic Cells", J. Exp. Med. 191(3): 411-416, (2000).
Taniguchi, et al., "High Prevalence of Autoantibodies Against Carbonic Anhydrase II and Lactoferrin in Type 1 Diabetes: Concept of Autoimmune Exocrinopathy and Endocrinopathy of the Pancreas", Pancreas 27(1): 26-30, 2003.
Ulmer, et al., "Gene-based vaccines: recent technical and clinical advances", Trends Mol Med. 12(5): 216-22, (2006).
Wallet, et al., "MerTK is required for apoptotic cell—induced T cell tolerance", J. Exp. Med. 205(1): 219-232 (2008).
Watson, et al., "'Pruning' of Alloreactive CD4+ T Cells Using 5-(and 6) Carboxyfluorescein Diacetate Succinimidyl Ester Prolongs Skin Allograft Survival", The Journal of Immunology, 173: 6574-6582, 2004.
Yamaguchi, et al., "The Effect of Pretreatment with Class I Major Histocompatibility Complex (MHC) Antigens on Hepatic or Cardiac Allograft Survival in the Rat", Transplant Proc. 21(3): 3355, Jun. 1989.

\* cited by examiner

SUBSTANCES, COMPOSITIONS AND METHODS FOR PREVENTING AND TREATING IMMUNE-MEDIATED INFLAMMATORY DISORDERS

CROSS-REFERENCE TO RELATED APPLICATION

The present Application is a 371 of International Patent Application PCT/US2006/17763 titled "Substances, Compositions and Methods for Preventing and Treating Immune-Mediated Inflammatory Disorders," filed May 5, 2006, which claims the benefit of U.S. provisional patent application 60/680,249, titled "Substances and Methods for Preventing and Treating Autoimmune Diseases," filed May 11, 2005, the contents of which are incorporated in this disclosure by reference in their entirety.

BACKGROUND

Immune-mediated inflammatory disorders (IMIDs) are a group of diseases that involve an immune response that is inappropriate or excessive, and is caused or accompanied by dysregulation of the organism normal cytokine milieu. IMIDs cause acute or chronic inflammatory injury in one or more than one organ system. IMIDs include allergies, asthma, the rejection of solid organ transplants, and autoimmune diseases, such as autoimmune hepatitis, multiple sclerosis, rheumatoid arthritis, Sjogren's syndrome, systemic lupus and vitiligo.

As an example, one IMID, type 1 diabetes or insulin-dependent diabetes mellitus, is one of the most frequent chronic diseases in children and adolescents, and has a steadily increasing worldwide prevalence and incidence. In a majority of cases, the onset of type 1 diabetes begins with the display by antigen presenting cells (APCs) of autoantigens synthesized by pancreatic β-cells. This display results in the immune system destruction of pancreatic beta cells mediated mostly by T helper 1 (Th1) and cytotoxic T lymphocytes. The specific destruction of β-cells results in loss of insulin production and causes the high morbidity and mortality associated with the disease.

Although daily insulin injection can ameliorate type 1 diabetes, it does not provide precise replacement of physiological levels of the hormone. A safe, potent, and practical approach to stop pathological autoimmunity could be used to reverse the disease by permitting β-cells to regenerate or regain function, and could also be used to prevent rejection of transplanted islets used as treatment for the disease.

Many prophylactic and therapeutic approaches for type 1 diabetes attempt to prevent the destruction of beta cells by inducing the immune system to delete, inactivate or suppress pathogenic self-reactive lymphocytes, such as by administering vaccines that solely deliver autoantigen, or by administering substances that are direct effectors of the immune system, such as cytokines. Currently available DNA-based vaccines, however, are not completely efficient in preventing and even less efficient in treating the disease, and the use of some of these vaccines is associated with inducing or enhancing autoimmunity rather than preventing the disease. Additionally, the use of cytokines is associated with significant morbidity because of their general suppression of the immune system.

Therefore, there is a need for a new method for preventing, delaying the onset of, or treating immune-mediated inflammatory disorders using substances or compositions that are not associated with these disadvantages. Further, there is a need for a new method for preventing, delaying the onset of, or treating immune-mediated inflammatory disorders that are not associated with these disadvantages.

SUMMARY

According to one embodiment of the present invention, there is provided a substance for preventing, delaying the onset of or treating one or more than one immune-mediated inflammatory disorder in an organism who is susceptible to developing the immune-mediated inflammatory disorder, who is developing the immune-mediated inflammatory disorder or who has the immune-mediated inflammatory disorder. The substance comprises a plasmid comprising a) a polynucleotide encoding an autoantigen or a donor antigen under the control of a promoter capable of promoting the polynucleotide encoding the autoantigen or the donor antigen; and b) a polynucleotide encoding a pro-apoptotic protein under the control of a promoter capable of promoting the polynucleotide encoding a pro-apoptotic protein; where the plasmid comprises a plurality of CpG motifs, and where at least some of the plurality of CpG motifs are methylated; and where the immune-mediated inflammatory disorder is caused by an immune response that is inappropriate or excessive or both inappropriate and excessive to the autoantigen or the donor antigen. In one embodiment, the promoter capable of promoting the polynucleotide encoding the autoantigen or the donor antigen, and the promoter capable of promoting the polynucleotide encoding a pro-apoptotic protein are a single promoter. In another embodiment, the plasmid further comprises an internal ribosome entry site sequence to permit translation of the polynucleotide encoding the autoantigen or the donor antigen, and the polynucleotide encoding a pro-apoptotic protein from the same transcript. In another embodiment, the internal ribosome entry site sequence is an internal ribosome binding site from the EMCV virus, SEQ ID NO:3. In one embodiment, the organism is a mammal. In another embodiment, the organism is a human. In another embodiment, the immune-mediated inflammatory disorder is selected from the group consisting of the rejection of solid organ transplants, autoimmune hepatitis, multiple sclerosis, rheumatoid arthritis, Sjogren's syndrome, systemic lupus, type I diabetes and vitiligo. In one embodiment, the polynucleotide 1) encodes the autoantigen or the donor antigen, or 2) encodes the pro-apoptotic protein, or 3) encodes the autoantigen or the donor antigen, and additionally encoding the pro-apoptotic protein, are selected from the group consisting of DNA and RNA. In another embodiment, the autoantigen is selected from the group consisting of carbonic anhydrase II, collagen, CYP2D6 (cytochrome P450, family 2, subfamily D, polypeptide 6), glutamic acid decarboxylase, secreted glutamic acid decarboxylase 55, SEQ ID NO:1, insulin, myelin basic protein and SOX-10 (SRY-box containing gene 10). In another embodiment, the pro-apoptotic protein is selected from the group consisting of BAX, SEQ ID NO:2, a modified caspase, Tumor Necrosis Factor Receptor, Death Receptor 3 (DR3), Death Receptor 4 (DR4), Death Receptor 5 (DR5) and a FAS receptor.

According to one embodiment of the present invention, there is provided a composition for preventing, delaying the onset of or treating one or more than one immune-mediated inflammatory disorder in an organism who is susceptible to developing the immune-mediated inflammatory disorder, who is developing the immune-mediated inflammatory disorder or who has the immune-mediated inflammatory disorder. The composition comprises a) a first plasmid comprising a polynucleotide encoding an autoantigen or a donor antigen under the control of a promoter capable of promoting the polynucleotide encoding the autoantigen or the donor antigen; and b) a second plasmid comprising a polynucleotide encoding a pro-apoptotic protein under the control of a promoter capable of promoting the polynucleotide encoding a pro-apoptotic protein; where the first plasmid comprises a plurality of CpG motifs, and at least some of the plurality of CpG motifs are methylated; and where the immune-mediated inflammatory disorder is caused by an immune response that is inappropriate or excessive or both inappropriate and excessive to the autoantigen or the donor antigen. In one embodiment, the second plasmid comprises a plurality of CpG motifs, and at least some of the plurality of CpG motifs are methylated. In one embodiment, the first plasmid and second plasmid are in a ratio of between 1/1000 to 1000/1. In another embodiment, the first plasmid and second plasmid are in a ratio of between 1/100 to 100/1. In another embodiment, the first plasmid and second plasmid are in a ratio of between 1/10 to 10/1. In one embodiment, the organism is a mammal. In another embodiment, the organism is a human. In one embodiment, the immune-mediated inflammatory disorder is selected from the group consisting of the rejection of solid organ transplants, autoimmune hepatitis, multiple sclerosis, rheumatoid arthritis, Sjogren's syndrome, systemic lupus, type I diabetes and vitiligo. In one embodiment, the polynucleotide 1) encodes the autoantigen or the donor antigen, or 2) encodes the pro-apoptotic protein, or 3) encodes the autoantigen or the donor antigen, and additionally encoding the pro-apoptotic protein, are selected from the group consisting of DNA and RNA. In one embodiment, the autoantigen is selected from the group consisting of carbonic anhydrase II, collagen, CYP2D6 (cytochrome P450, family 2, subfamily D, polypeptide 6), glutamic acid decarboxylase, secreted glutamic acid decarboxylase 55, SEQ ID NO:1, insulin, myelin basic protein and SOX-10 (SRY-box containing gene 10). In one embodiment, the pro-apoptotic protein is selected from the group consisting of BAX, SEQ ID NO:2, a modified caspase, Tumor Necrosis Factor Receptor, Death Receptor 3 (DR3), Death Receptor 4 (DR4), Death Receptor 5 (DR5) and a FAS receptor.

According to one embodiment of the present invention, there is provided a method of preventing, delaying the onset of or treating an organism who is susceptible to developing the immune-mediated inflammatory disorder, who is developing the immune-mediated inflammatory disorder or who has the immune-mediated inflammatory disorder. In one embodiment, the method comprises a) selecting an organism who is susceptible to developing the immune-mediated inflammatory disorder, who is developing the immune-mediated inflammatory disorder or who has the immune-mediated inflammatory disorder; and b) administering to the organism one or more than one dose of a substance according to the present invention. In another embodiment, the method comprises a) selecting an organism who is susceptible to developing the immune-mediated inflammatory disorder, who is developing the immune-mediated inflammatory disorder or who has the immune-mediated inflammatory disorder; and b) administering to the organism one or more than one dose of a composition according to the present invention. In one embodiment, the first plasmid and the second plasmid are administered sequentially. In another embodiment, the first plasmid and the second plasmid are administered simultaneously. In one embodiment, the immune-mediated inflammatory disorder is selected from the group consisting of the rejection of solid organ transplants, autoimmune hepatitis, multiple sclerosis, rheumatoid arthritis, Sjogren's syndrome, systemic lupus, type I diabetes and vitiligo. In another embodiment, the one or more than one dose is a plurality of doses. In one embodiment, the dose is between about 0.001 mg/Kg of body weight of the organism and about 100 mg/Kg of body weight of the organism. In another embodiment, the dose is between about 0.01 mg/Kg of body weight of the organism and about 10 mg/Kg of body weight of the organism. In another embodiment, the dose is between about 0.1 mg/Kg of body weight of the organism and about 1 mg/Kg of body weight of the organism. In one embodiment, the dose is administered weekly between 2 times and about 100 times. In another embodiment, the dose is administered weekly between 2 times and about 20 times. In another embodiment, the dose is administered weekly between 2 times and about 10 times. In one embodiment, administering the one or more than one dose to the organism is performed by a route selected from the group consisting of epidermal, intradermal, intramuscular, intranasal, intravenous and oral. In one embodiment, the method further comprises monitoring the organism for the development or progression of the immune-mediated inflammatory disorder. In a preferred embodiment, monitoring the organism comprises testing the organism for levels of antibodies to the autoantigen or the donor antigen, where decreasing levels of antibodies signifies successfully preventing the immune-mediated inflammatory disorder, delaying the onset of the immune-mediated inflammatory disorder or treating the organism for immune-mediated inflammatory disorder. In a particularly preferred embodiment, the autoantigen is selected from the group consisting of carbonic anhydrase II, collagen, CYP2D6 (cytochrome P450, family 2, subfamily D, polypeptide 6), glutamic acid decarboxylase, secreted glutamic acid decarboxylase 55, SEQ ID NO:1, insulin, myelin basic protein and SOX-10 (SRY-box containing gene 10).

According to another embodiment of the present invention, there is provided use of the substance according to the present invention, for preventing, delaying the onset of or treating one or more than one immune-mediated inflammatory disorder in an organism who is susceptible to developing the immune-mediated inflammatory disorder, who is developing the immune-mediated inflammatory disorder or who has the immune-mediated inflammatory disorder.

According to another embodiment of the present invention, there is provided use of the composition according to the present invention, for preventing, delaying the onset of or treating one or more than one immune-mediated inflammatory disorder in an organism who is susceptible to developing the immune-mediated inflammatory disorder, who is developing the immune-mediated inflammatory disorder or who has the immune-mediated inflammatory disorder.

FIGURES

These and other features, aspects and advantages of the present invention will become better understood with regard to the following description, appended claims, and accompanying figures where:

Figure 11:
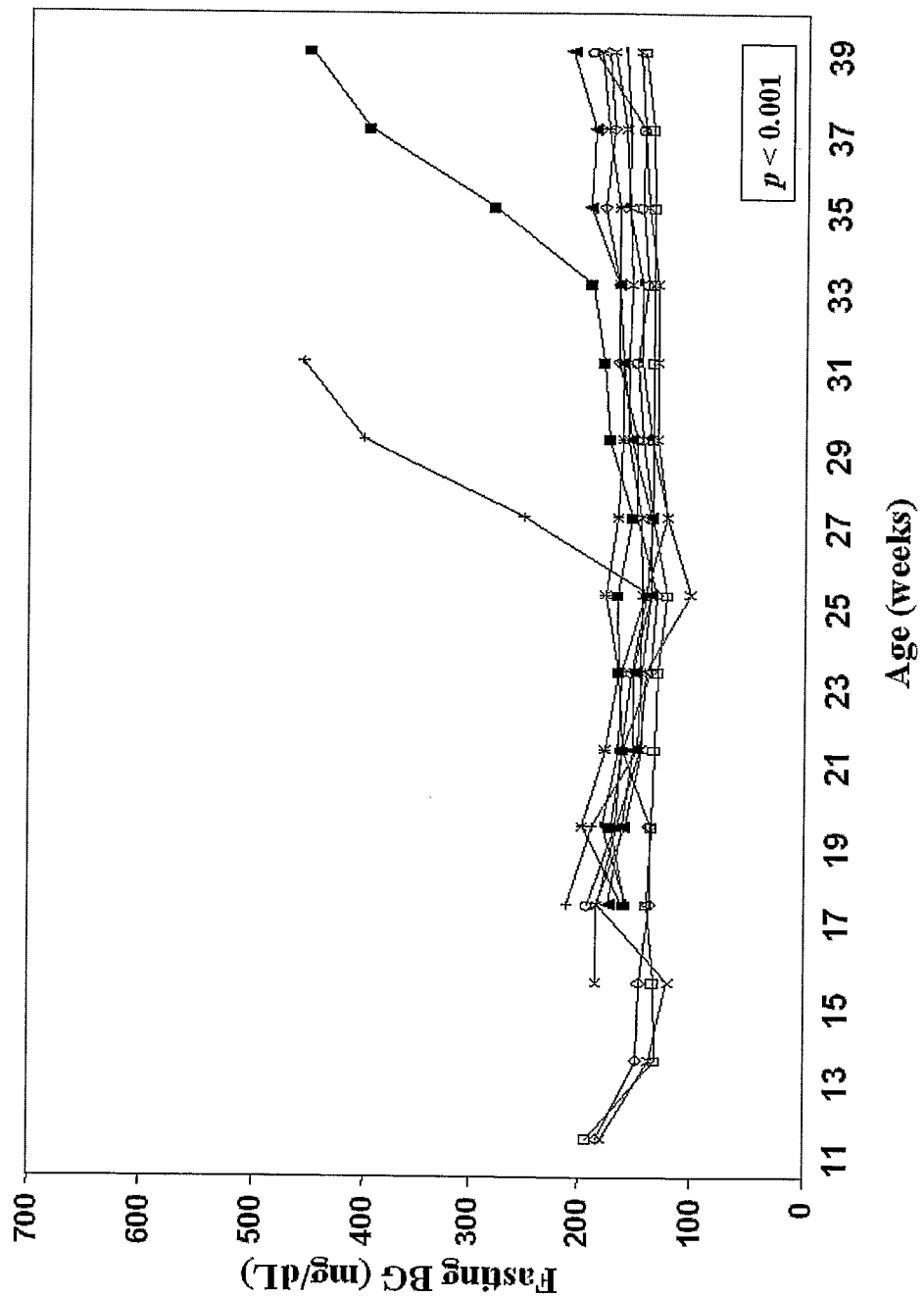
Figure 12:
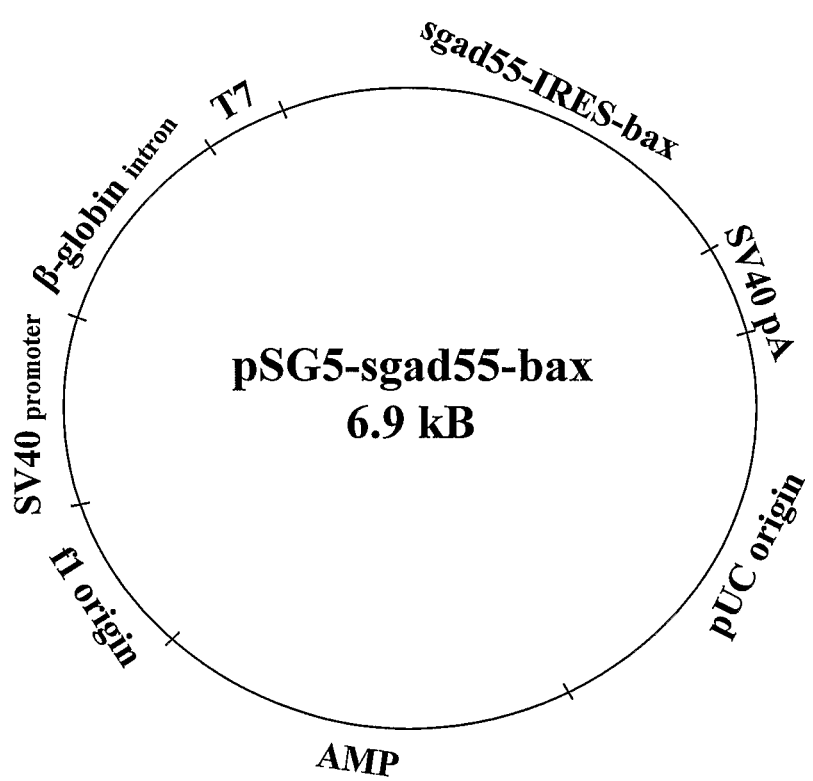

FIG. 11 and is a graph plotting the fasting blood glucose level versus the age of individual NOD mice for the Group 7 treated with 40 μg of Plasmid 5 and 10 μg of Plasmid 6 (a composition according to the present invention); and FIG. 12 is a schematic depiction of a substance according to the present invention for preventing, delaying the onset of or treating one or more than one immune-mediated inflammatory disorder in an organism who is susceptible to developing the immune-mediated inflammatory disorder, who is developing the immune-mediated inflammatory disorder or who has the immune-mediated inflammatory disorder.

DESCRIPTION

According to one embodiment of the present invention, there is provided a substance or a composition for preventing, delaying the onset of or treating one or more than one immune-mediated inflammatory disorder in an organism who is susceptible to developing the immune-mediated inflammatory disorder, who is developing the immune-mediated inflammatory disorder or who has the immune-mediated inflammatory disorder. According to another embodiment of the present invention, there is provided a method of preventing, delaying the onset of or treating an organism who is susceptible to developing the immune-mediated inflammatory disorder, who is developing the immune-mediated inflammatory disorder or who has the immune-mediated inflammatory disorder. In one embodiment, the method comprises administering to the organism a substance or a composition according to the present invention.

As used in this disclosure, the term "comprise" and variations of the term, such as "comprising" and "comprises," are not intended to exclude other additives, components, integers or steps.

As used in this disclosure, the term "autoantigen" comprises an endogenous antigen that stimulates the production of autoantibodies, as in an autoimmune reaction, as well as part of such endogenous antigens, or modified endogenous antigens that elicit the same response as the full endogenous antigen, as will be understood by those with skill in the art with reference to this disclosure. For example, in the context of this disclosure secreted glutamic acid decarboxylase 55 and humanized BAX are both autoantigens.

As used in this disclosure, the term "donor antigen" comprises an antigen from an allograft that was transplanted into the organism to take the place of defective or absent cells or tissues, such as for example islet cell transplants, and partial or whole organ transplants including transplanted hearts, lungs, kidneys and livers, and that stimulates the production of antibodies that produce an immune reaction, as well as part of such donor antigens, or modified donor antigens that elicit the same response as the full donor antigen, as will be understood by those with skill in the art with reference to this disclosure.

As used in this disclosure, the term "immune-mediated inflammatory disorders" comprises both diseases due in part or in total to destruction of normal cells or tissues by the immune system of the organism, and also comprises destruction by the immune system of the organism of cells or tissues (allografts) that were transplanted into the organism to take the place of defective or absent cells or tissues, such as for example islet cell transplants, and partial or whole organ transplants including transplanted hearts, lungs, kidneys and livers.

As used in this disclosure, the term "hBAX" and "BAX" are interchangeable.

A CpG motif is a polynucleotide region characterized by cytosine residues in the sequence CG that stimulates the immune system in mammals to start a sequence of reactions leading to an immune reaction and inflammation.

As will be understood by those with skill in the art with reference to this disclosure, when reference is made to a protein encoded by a polynucleotide sequence, the protein includes "conservative substitutions" in which an amino acid is substituted for another amino acid that has similar properties, such that one skilled in the art of peptide chemistry would expect the secondary structure and hydropathic nature of the polypeptide to be substantially unchanged. A conservative substitution occurs when one amino acid residue is replaced with another that has a similar side chain. Amino acid residues having similar side chains are known in the art and include families with basic side chains (e.g., lysine (Lys/K), arginine (Arg/R), histidine (His/H)), acidic side chains (e.g., aspartic acid (Asp/D), glutamic acid (Glu/E)), uncharged polar side chains (e.g., glycine (Gly/G), asparagine (Asn/N), glutamine (Gln/Q), serine (Ser/S), threonine (Thr/T), tyrosine (Tyr/Y), cysteine (Cys/C)), nonpolar side chains (e.g., alanine (Ala/A), valine (Val/V), leucine (Leu/L), isoleucine (Ile/I), proline (Pro/P), phenylalanine (Phe/F), methionine (Met/M), tryptophan (Trp/W)), β-branched side chains (e.g., threonine (Thr/T), valine (Val/V), isoleucine (Ile/I)) and aromatic side chains (e.g., tyrosine (Tyr/Y), phenylalanine (Phe/F), tryptophan (Trp/W), histidine (His/H)).

Advantageously, the substances and compositions of the present invention are polynucleotide based and can be produced in large quantities at relatively low cost and do not require a "cold chain" for storage. Advantageously, the method of the present invention uses a substance or a composition to induce apoptosis of one or more than one type of cell which in turn induces immunosuppressive regulatory T cells, rather than direct effectors of the immune system such as cytokines. Therefore, the present method is associated with less risk of inducing or enhancing autoimmunity as compared to some prior art methods because these one or more than one type of cells capable of suppressing the immune-mediated inflammatory disorder are still subject to physiological and immune regulation. Further advantageously, the present method comprises administering to the organism a substance or composition that supplies genetic material to the organism, thereby modifying the genetic material of the organism directly and permitting the native epitopes to be processed by the immune system of the organism, unlike methods comprising administering to the organism a protein-based substance or composition. Therefore, the substances, compositions and methods according to the present invention are economical and practical for use in preventing, delaying the onset of or treating an organism who is susceptible to developing the immune-mediated inflammatory disorder, who is developing the immune-mediated inflammatory disorder or who has the immune-mediated inflammatory disorder. The substances, compositions, and the methods of the present invention will now be disclosed in detail.

According to one embodiment of the present invention, there is provided a substance for preventing, delaying the onset of or treating one or more than one immune-mediated inflammatory disorder in an organism who is susceptible to developing the immune-mediated inflammatory disorder, who is developing the immune-mediated inflammatory disorder or who has the immune-mediated inflammatory disorder, where the immune-mediated inflammatory disorder is caused at least in part by an immune response of the organism to an autoantigen, or to a donor antigen in the case of allograft transplantation. The substance of the present invention comprises a plasmid comprising a polynucleotide encoding an autoantigen or a donor antigen under the control of a promoter capable of promoting the polynucleotide encoding the autoantigen or the donor antigen, and further comprises a polynucleotide encoding a pro-apoptotic protein under the control of a promoter capable of promoting the polynucleotide encoding a pro-apoptotic protein, where the plasmid comprises a plurality of CpG motifs, and where at least some of the plurality of CpG motifs are methylated, where the immune-mediated inflammatory disorder is caused by an immune response that is inappropriate or excessive or both inappropriate and excessive to the autoantigen or the donor antigen. In a preferred embodiment, the promoter capable of promoting the polynucleotide encoding the autoantigen or the donor antigen, and the promoter capable of promoting the polynucleotide encoding a pro-apoptotic protein are a single promoter. In a preferred embodiment, the promoter capable of promoting the polynucleotide encoding the autoantigen or the donor antigen, or the promoter capable of promoting the polynucleotide encoding a pro-apoptotic protein, or both the promoter capable of promoting the polynucleotide encoding the autoantigen or the donor antigen, and the promoter capable of promoting the polynucleotide encoding a pro-apoptotic protein maintain their promoter function after methylation. In another embodiment, the plasmid comprises an internal ribosome entry site (IRES) sequence to permit translation of the polynucleotide encoding the autoantigen or the donor antigen, and the polynucleotide encoding a pro-apoptotic protein from the same transcript.

In another embodiment, the present invention is a composition comprising a first plasmid and a second plasmid. The first plasmid comprises a polynucleotide encoding an autoantigen or a donor antigen under the control of a promoter capable of promoting the polynucleotide encoding the autoantigen or the donor antigen. The second plasmid comprises a polynucleotide encoding a pro-apoptotic protein under the control of a promoter capable of promoting the polynucleotide encoding a pro-apoptotic protein. The first plasmid comprises a plurality of CpG motifs, and at least some of the plurality of CpG motifs are methylated. The immune-mediated inflammatory disorder is caused by an immune response that is inappropriate or excessive or both inappropriate and excessive to the autoantigen or the donor antigen. In a preferred embodiment, the promoter capable of promoting the polynucleotide encoding the autoantigen or the donor antigen maintains its promoter function after methylation. In another embodiment, the second plasmid comprises a plurality of CpG motifs, and at least some of the plurality of CpG motifs are methylated. In a preferred embodiment, the promoter capable of promoting the polynucleotide encoding a pro-apoptotic protein maintains its promoter function after methylation. In one embodiment, the composition comprises the first plasmid and second plasmid in a ratio of between 1/1000 to 1000/1. In another embodiment, the composition comprises the first plasmid and second plasmid in a ratio of between 1/100 to 100/1. In another embodiment, the composition comprises the first plasmid and second plasmid in a ratio of between 1/10 to 10/1.

In one embodiment of the present invention, the organism is a mammal. In another embodiment, the organism is a human. In one embodiment, the immune-mediated inflammatory disorder is selected from the group consisting of the rejection of solid organ transplants, autoimmune hepatitis, multiple sclerosis, rheumatoid arthritis, Sjogren's syndrome, systemic lupus, type I diabetes and vitiligo. In another embodiment, the polynucleotide 1) encodes the autoantigen or the donor antigen, or 2) encodes the pro-apoptotic protein, or 3) encodes the autoantigen or the donor antigen, and additionally encoding the pro-apoptotic protein, are selected from the group consisting of DNA and RNA. In another embodiment, the autoantigen is selected from the group consisting of carbonic anhydrase II, collagen, CYP2D6 (cytochrome P450, family 2, subfamily D, polypeptide 6), glutamic acid decarboxylase, secreted glutamic acid decarboxylase 55, SEQ ID NO:1, insulin, myelin basic protein and SOX-10 (SRY-box containing gene 10). In another embodiment, the pro-apoptotic protein is selected from the group consisting of BAX, SEQ ID NO:2, a modified caspase, Tumor Necrosis Factor Receptor, Death Receptor 3 (DR3), Death Receptor 4 (DR4), Death Receptor 5 (DR5) and a FAS receptor. In a preferred embodiment, the internal ribosome entry site sequence is an internal ribosome binding site from the EMCV virus, SEQ ID NO:3.

According to another embodiment of the present invention, there is provided a method of preventing, delaying the onset of or treating an organism who is susceptible to developing the immune-mediated inflammatory disorder, who is developing the immune-mediated inflammatory disorder or who has the immune-mediated inflammatory disorder. In one embodiment, the method comprises administering to the organism a substance or a composition according to the present invention.

In one embodiment, the method comprises, first, selecting an organism who is susceptible to developing the immune-mediated inflammatory disorder, who is developing the immune-mediated inflammatory disorder or who has the immune-mediated inflammatory disorder. The selection can be made using standard methods as will be understood by those with skill in the art with reference to this disclosure. For example, if the immune-mediated inflammatory disorder is multiple sclerosis, the selection can be made by identifying in the patient the presence of demyelination lesions in the central nervous system at different times using CAT scans or magnetic resonance imaging (MRI). Similarly, if the immune-mediated inflammatory disorder is diabetes, the selection can be made by identifying in the patient the presence of anti-insulin or anti-GAD autoantibodies or both anti-insulin and/or anti-GAD autoantibodies, the presence of increasing hyperglycemia, the presence of glycosuria, the presence of a genetic predisposition to diabetes or more than one of these.

The method comprises administering to the organism one or more than one dose of a substance. or a composition according to the present invention. In a preferred embodiment, the substance or composition is administered in a plurality of doses. In another preferred embodiment, the dose is between about 0.001 mg/Kg of body weight of the organism and about 100 mg/Kg of body weight of the organism. In another preferred embodiment, the dose is between about 0.01 mg/Kg of body weight of the organism and about 10 mg/Kg of body weight of the organism. In another preferred embodiment, the dose is between about 0.1 mg/Kg of body weight of the organism and about 1 mg/Kg of body weight of the organism. In another preferred embodiment, the dose is about 0.05 mg/Kg of body weight of the organism. In a preferred embodiment, the organism is a human and the dose is between about 0.5 mg and 5 mg. In another preferred embodiment, the organism is a human and the dose is between about 1 mg and 4 mg. In another preferred embodiment, the organism is a human and the dose is between about 2.5 mg and 3 mg. In another preferred embodiment, the dose is administered weekly between 2 times and about 100 times. In another preferred embodiment, the dose is administered weekly between 2 times and about 20 times. In another preferred embodiment, the dose is administered weekly between 2 times and about 10 times. In another preferred embodiment, the dose is administered weekly 4 times. In another preferred embodiment, the dose is administered only once.

Administering the one or more than one dose of a substance or a composition to the organism can be accomplished by any suitable route, as will be understood by those with skill in the art with reference to this disclosure. In a preferred embodiment, administering to the organism one or more than one dose of a substance or a composition is performed by a route selected from the group consisting of epidermal, intradermal, intramuscular, intranasal, intravenous and oral.

When the method comprises administering a composition of the present invention, the first plasmid and the second plasmid can be administered either sequentially or simultaneously, as will be understood by those with skill in the art with reference to this disclosure.

In one embodiment, the method further comprises, after administering, monitoring the organism for the development or progression of the immune-mediated inflammatory disorder. In one embodiment, monitoring the organism comprises testing the organism for levels of antibodies to the autoantigen or the donor antigen, where decreasing levels of antibodies signifies successfully preventing the immune-mediated inflammatory disorder, delaying the onset of the immune-mediated inflammatory disorder or treating the organism for immune-mediated inflammatory disorder. In another embodiment, where the immune-mediated inflammatory disorder is rheumatoid arthritis, monitoring the organism comprises testing the organism for fatigue, lack of appetite, low grade fever, muscle and joint aches, and stiffness. In another embodiment, where the immune-mediated inflammatory disorder is type I diabetes, monitoring the organism comprises testing the organism for blood glucose levels, where decreasing levels of blood glucose signifies successfully preventing the immune-mediated inflammatory disorder, delaying the onset of the immune-mediated inflammatory disorder or treating the organism for autoimmune disease. In one embodiment, where the immune-mediated inflammatory disorder is type I diabetes, monitoring the organism comprises testing the organism for levels of glucosuria, where decreasing levels of glucosuria signifies successfully preventing the immune-mediated inflammatory disorder, delaying the onset of the immune-mediated inflammatory disorder or treating the organism for autoimmune disease.

EXAMPLE I

According to the present invention, the onset of diabetes in a mammal was prevented, delayed or prior existing diabetes was treated as follows. The mammals used in this example, female non-obese diabetic (NOD) mice, is the animal model most often used as a surrogate for testing approaches for both the suppression of type 1 diabetes and for the suppression of other autoimmune diseases in humans. Successful approaches in this animal model are generally predictive of success in humans.

Figure 1:
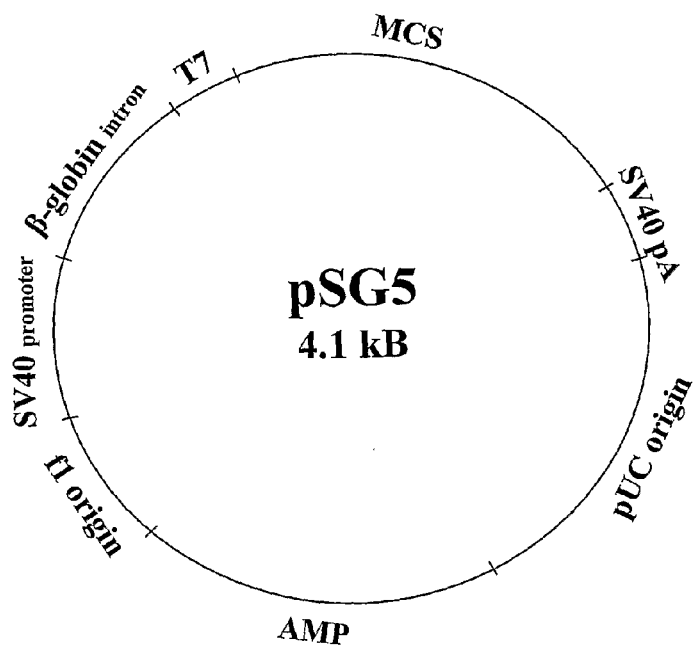
FIG. 1 is a schematic depiction of pSG5, Plasmid 1, where Plasmid 2 is the methylated form of Plasmid 1.
Figure 2:
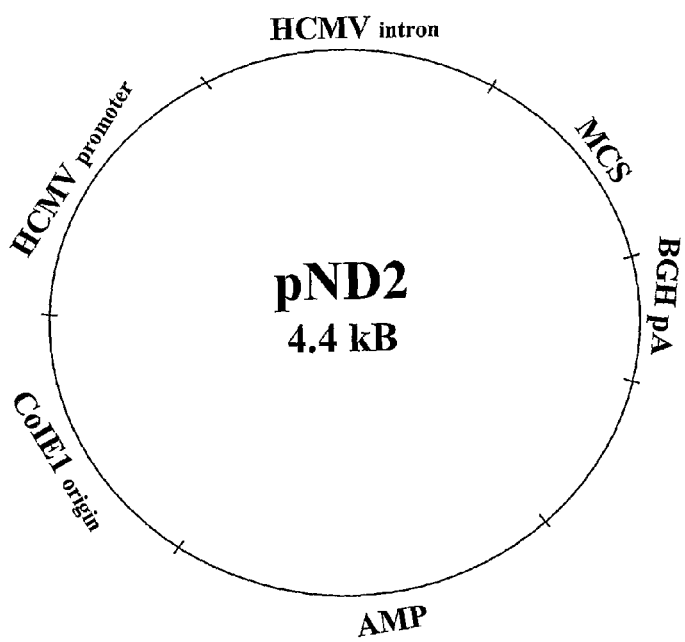
FIG. 2 is a schematic depiction of pND2, Plasmid 3.
Figure 3:
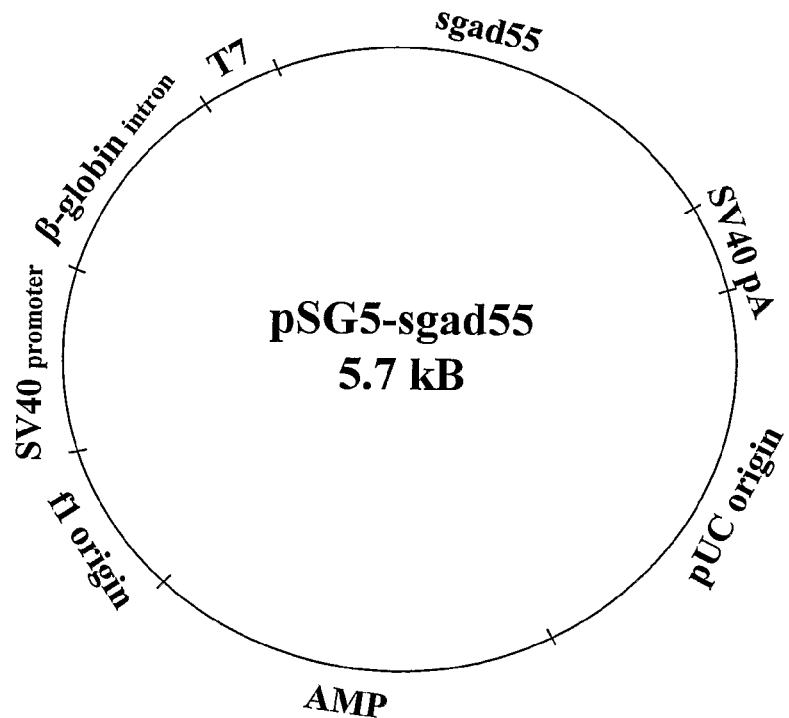
FIG. 3 is a schematic depiction of pSG5-SGAD55, Plasmid 4, where Plasmid 5 is the methylated form of Plasmid 4.
Figure 4:
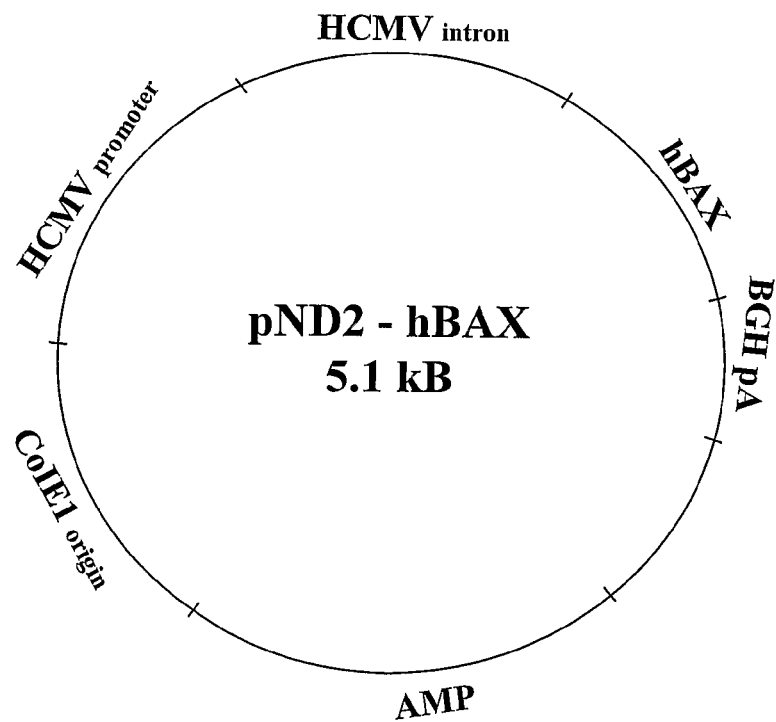
FIG. 4 is a schematic depiction of pND2-hBAX, Plasmid 6.
Figure 5:
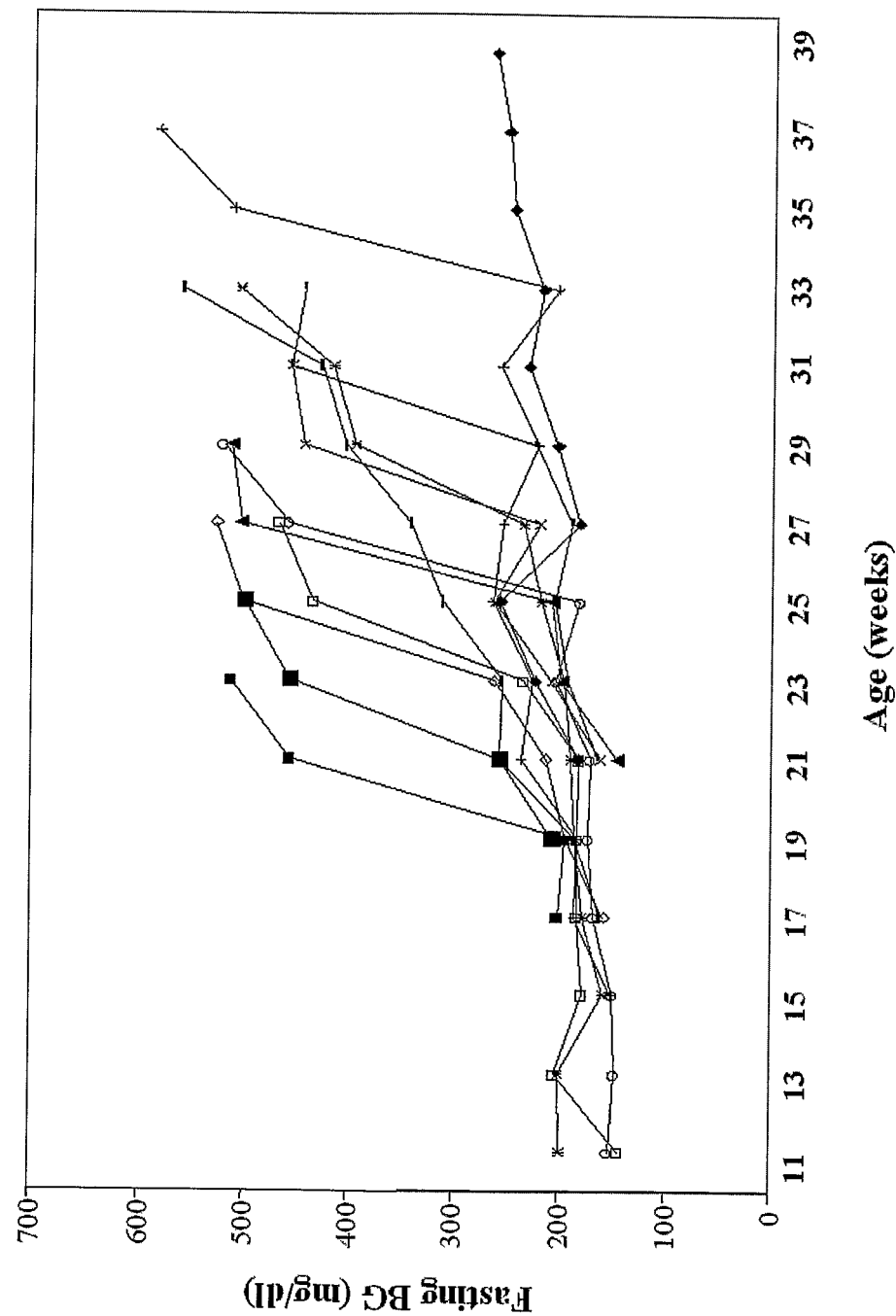
FIG. 5 is a graph plotting the fasting blood glucose level versus the age of individual NOD mice for the Group 1, the control group.
Figure 6:
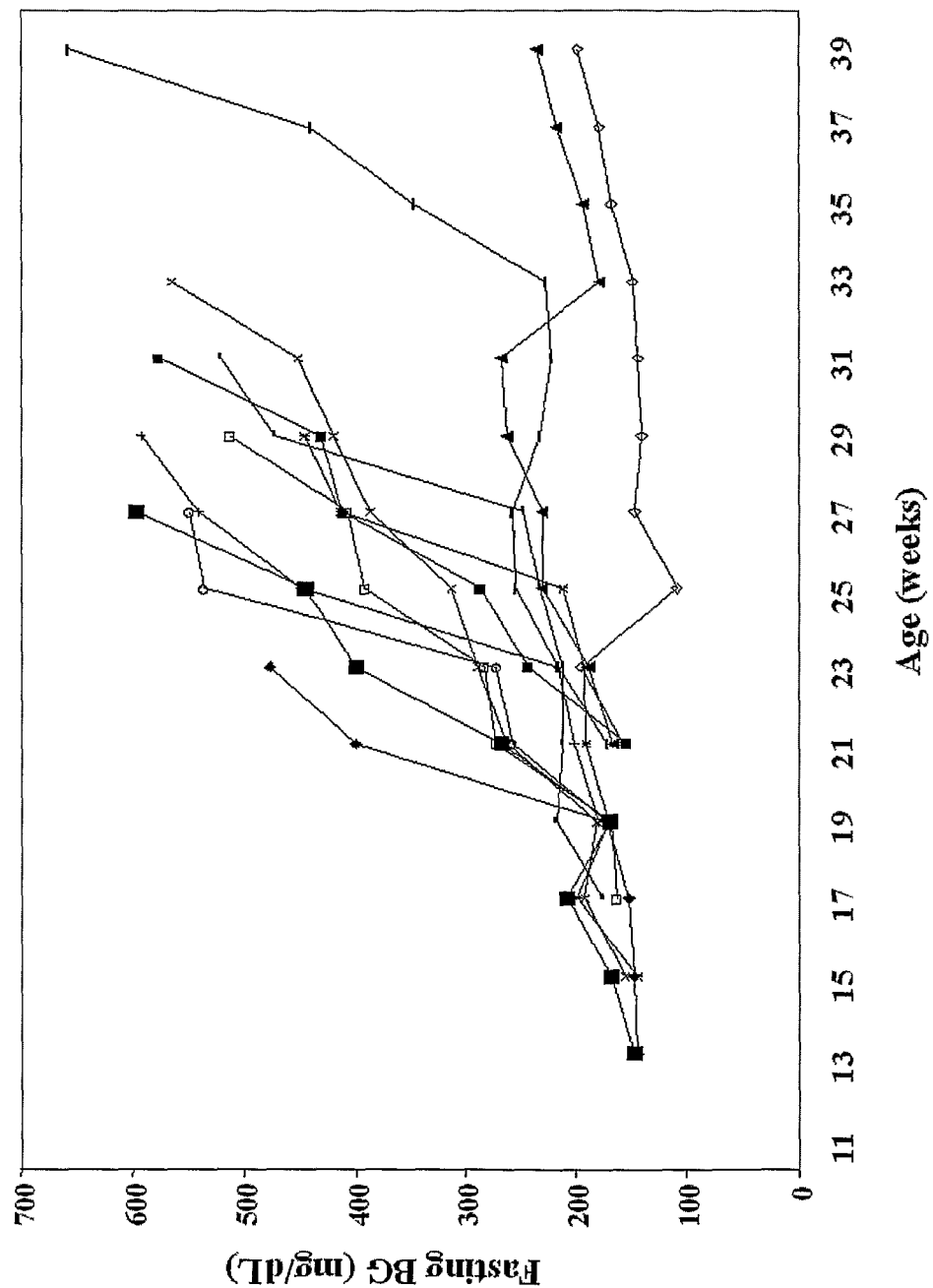
FIG. 6 is a graph plotting the fasting blood glucose level versus the age of individual NOD mice for the Group 2 treated with 40 μg of Plasmid 1 and 10 μg of Plasmid 3 (the vector control group)
Figure 7:
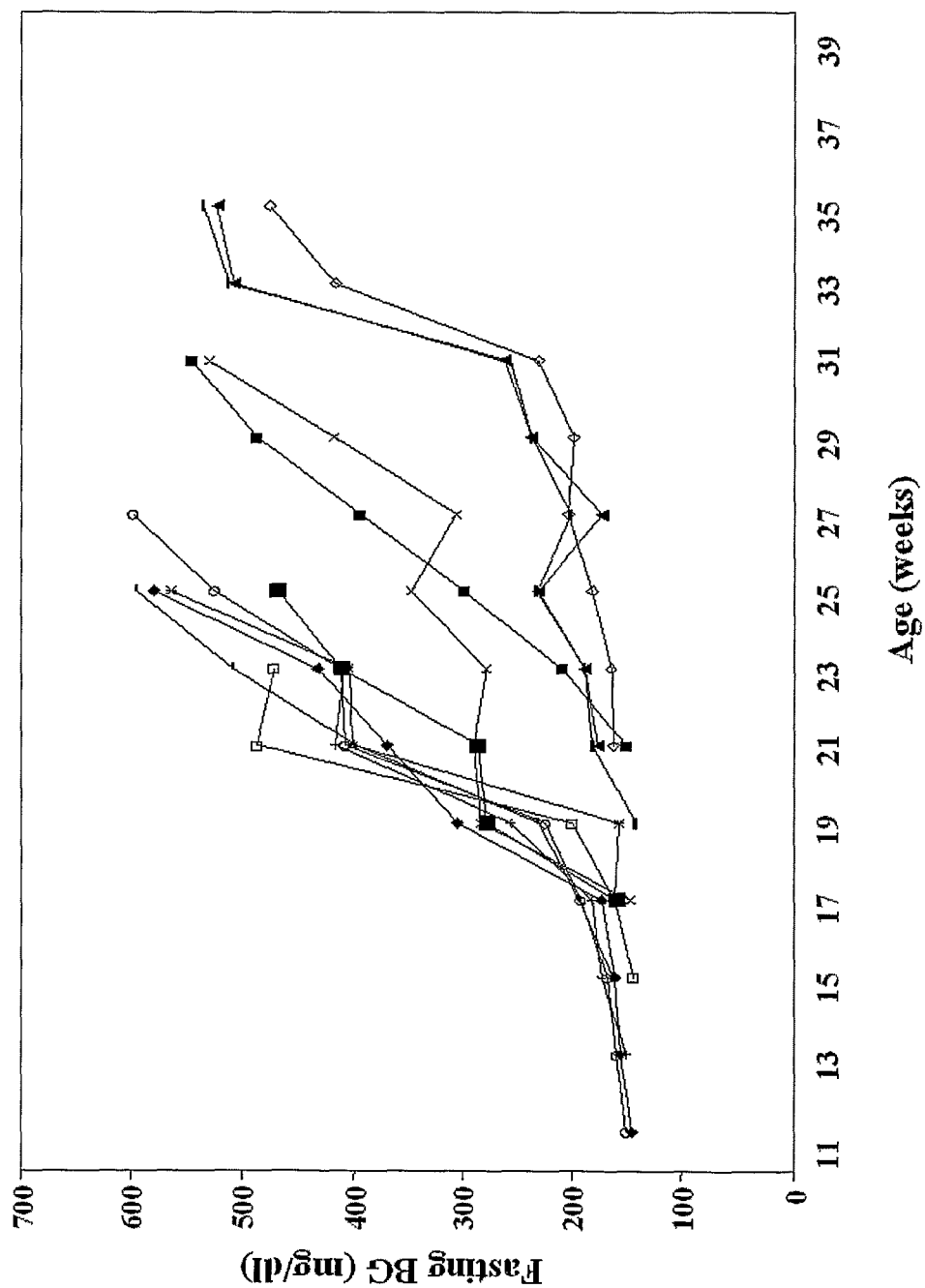
FIG. 7 is a graph plotting the fasting blood glucose level versus the age of individual NOD mice for the Group 3 treated with 40 μg of Plasmid 2 and 10 μg of Plasmid 3.
Figure 8:
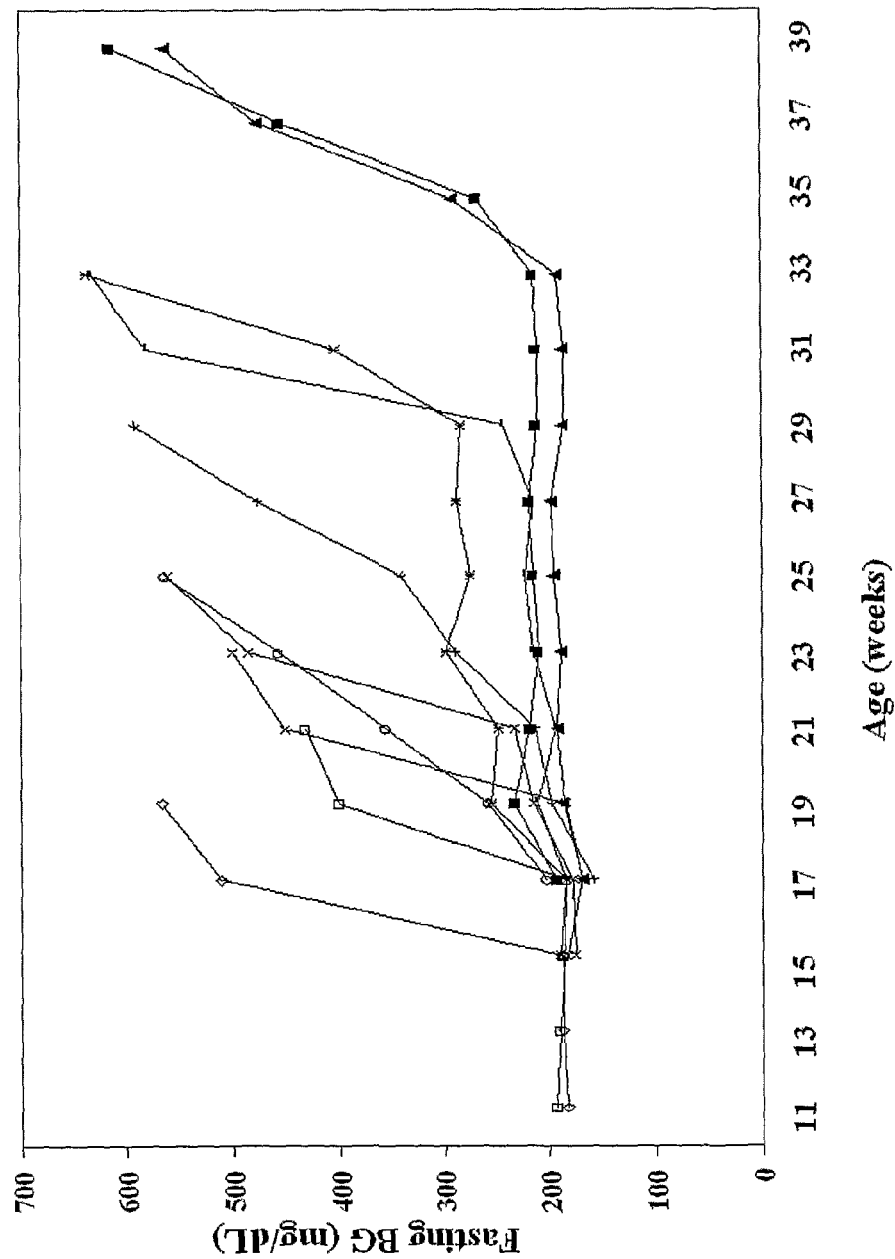
FIG. 8 is a graph plotting the fasting blood glucose level versus the age of individual NOD mice for the Group 4 treated with 40 μg of Plasmid 5 and 10 μg of Plasmid 3.
Figure 9:
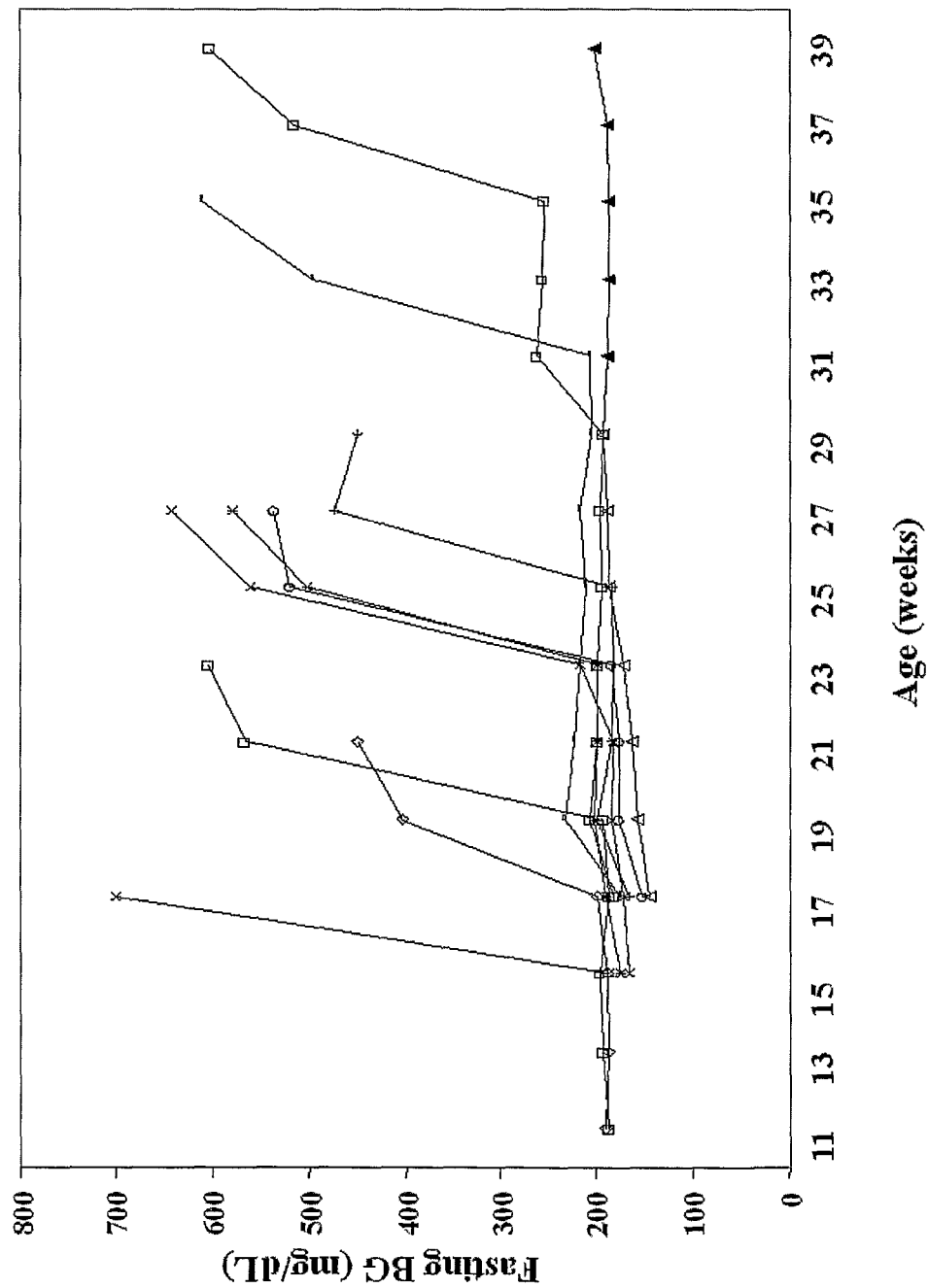
FIG. 9 is a graph plotting the fasting blood glucose level versus the age of individual NOD mice for the Group 5 treated with 40 μg of Plasmid 2 and 10 μg of Plasmid 6.
Figure 10:
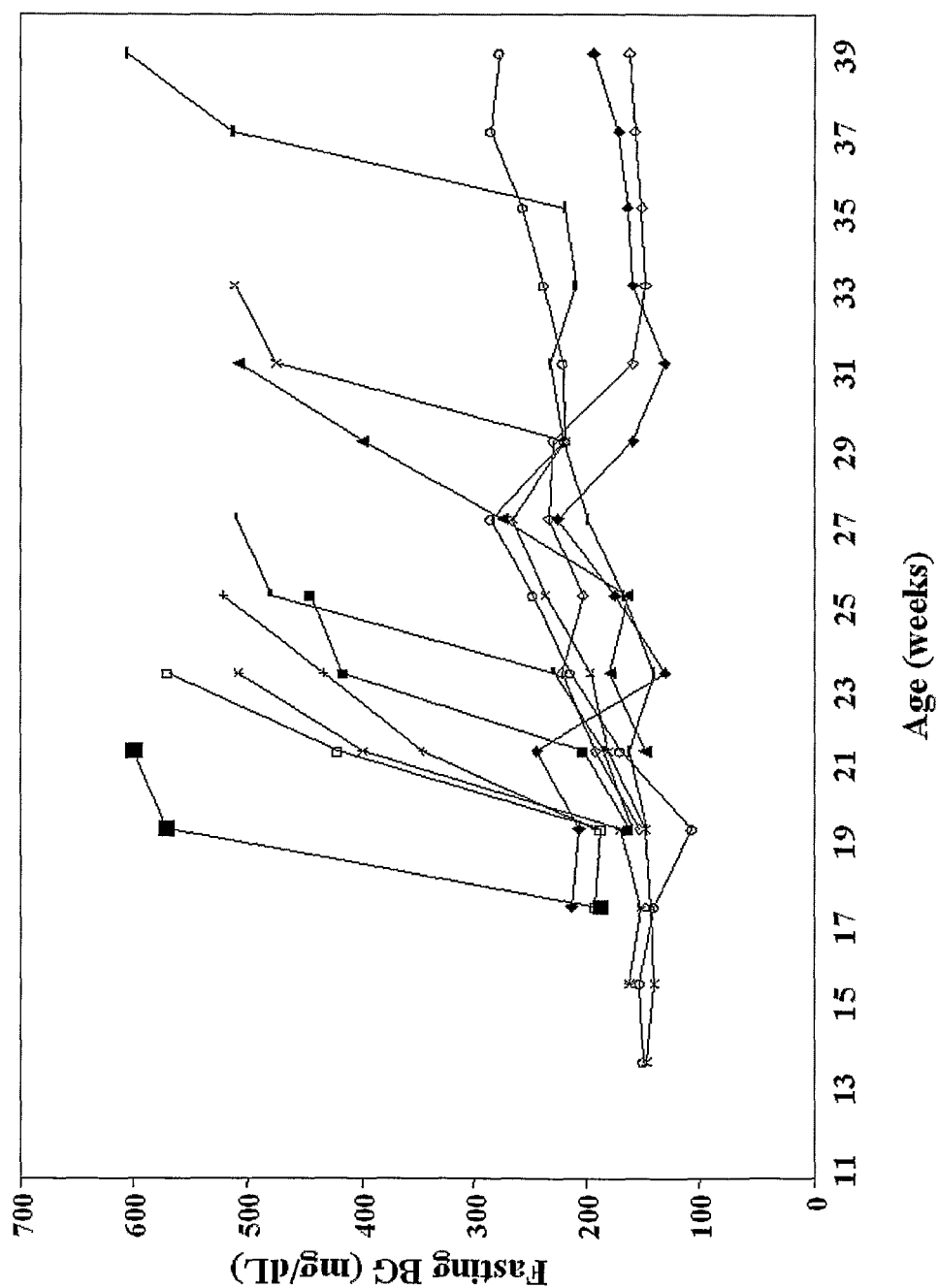
FIG. 10 is a graph plotting the fasting blood glucose level versus the age of individual NOD mice for the Group 6 treated with 40 μg of Plasmid 4 and 10 μg of Plasmid 6.

In order to compare the efficacy of a composition for preventing, delaying the onset of or treating one or more than one immune-mediated inflammatory disorder according to the present invention in an organism who is susceptible to developing the immune-mediated inflammatory disorder, who is developing the immune-mediated inflammatory disorder or who has the immune-mediated inflammatory disorder, six plasmids were prepared. Referring now to FIG. 1 through FIG. 4, there are shown, respectively, a schematic depiction of pSG5, Plasmid 1, where Plasmid 2 is the methylated form of Plasmid 1 (FIG. 1); a schematic depiction of pND2, Plasmid 3 (FIG. 2); a schematic depiction of pSG5-SGAD55, Plasmid 4, where Plasmid 5 is the methylated form of Plasmid 4 (FIG. 3); and a schematic depiction of pND2-hBAX, Plasmid 6 (FIG. 4).

Plasmid 1 was purchased from Stratagene (San Diego, Calif. US). The remaining plasmids were produced using standard techniques. pSG5, Plasmid 1, and pSG-SGAD55, Plasmid 4, were methylated to produce methylated pSG5, Plasmid 2, and methylated pSG5-SGAD55, Plasmid 5, by amplification in an $E.\ coli$ strain carrying a plasmid encoding the SssI methylase (New England Biolabs, Beverly, Mass. US). SssI methylates the dinucleotide motif CpG in DNA in a manner corresponding to mammalian methylases by covalently adding a single methyl group to the dinucleotide motif CpG. Successful methylation was confirmed by digesting the isolated plasmid DNA with the restriction enzyme HpaII which digests unmethylated but not methylated DNA, where resistance to HpaII digestion indicates successful methylation.

With reference to FIG. 1 through FIG. 4, the abbreviations shown are standard, as will be understood by those with skill in the art with reference to this disclosure, including: AMP (ampicillin resistance gene for selection in $E.\ coli$); BGH pA (bovine growth hormone polyadenylation sequence); ColE1 origin (origin of replication in $E.\ coli$); f1 origin (origin of replication for filamentous phage f1 to generate single stranded DNA); hBAX (human bax cDNA), SEQ ID NO: 2; HCMV promoter (promoter from cytomegalovirus); HCMV intron (intron from cytomegalovirus); MCS (multiple cloning site); pUC origin (origin of replication for $E.\ coli$ form pUC plasmid); sgad55 (secreted GAD cDNA construct), SEQ ID NO:1; SV40 promoter (simian virus 40 promoter); SV40 pA (simian virus 40 polyadenylation sequence); and T7 (T7 promoter).

Seven groups of female NOD mice (10-12 mice/group) were monitored for diabetes (defined as fasting blood glucose >140 mg/dL) from the age of 10 weeks. One group was left untreated as control. The other 6 groups received four ventral skin, intradermal injections of 50 μg of plasmid total at time of diabetes onset and then one additional injection each week for the next three weeks. The mice were monitored and those mice that did not respond, or that responded but relapsed received a second set of four injections of 50 μg of plasmid total, one injection per week when fasting blood glucose were >140 mg/dL. The 7 groups of mice were administered plasmids as follows:

Group 1: no administration (control group)
Group 2: 40 μg of Plasmid 1 and 10 μg of Plasmid 3 (the vector control group)
Group 3: 40 μg of Plasmid 2 and 10 μg of Plasmid 3
Group 4: 40 μg of Plasmid 5 and 10 μg of Plasmid 3

Group 5: 40 µg of Plasmid 2 and 10 µg of Plasmid 6
Group 6: 40 µg of Plasmid 4 and 10 µg of Plasmid 6
Group 7: 40 µg of Plasmid 5 and 10 µg of Plasmid 6 (a composition according to the present invention)

Referring now to FIG. 5 through FIG. 11, there are shown, respectively, a graph plotting the fasting blood glucose level versus the age of individual NOD mice for the Group 1, the control group (FIG. 5); a graph plotting the fasting blood glucose level versus the age of individual NOD mice for the Group 2 treated with 40 µg of Plasmid 1 and 10 µg of Plasmid 3 (the vector control group) (FIG. 6); a graph plotting the fasting blood glucose level versus the age of individual NOD mice for the Group 3 treated with 40 µg of Plasmid 2 and 10 µg of Plasmid 3 (FIG. 7); a graph plotting the fasting blood glucose level versus the age of individual NOD mice for the Group 4 treated with 40 µg of Plasmid 5 and 10 µg of Plasmid 3 (FIG. 8); a graph plotting the fasting blood glucose level versus the age of individual NOD mice for the Group 5 treated with 40 µg of Plasmid 2 and 10 µg of Plasmid 6 (FIG. 9); a graph plotting the fasting blood glucose level versus the age of individual NOD mice for the Group 6 treated with 40 µg of Plasmid 4 and 10 µg of Plasmid 6 (FIG. 10); and a graph plotting the fasting blood glucose level versus the age of individual NOD mice for the Group 7 treated with 40 µg of Plasmid 5 and 10 µg of Plasmid 6 (a composition according to the present invention) (FIG. 11).

As can be seen in the Figures, the methylation alone (FIG. 7), methylation and the presence of SGAD55 alone, methylation and the presence of BAX alone (FIG. 9), and the presence of SGAD55 and BAX alone (FIG. 10), do not delay the onset, prevent or treat diabetes. As can be seen in FIG. 11, however, methylation and the presence of SGAD55 and BAX delays the onset, prevents or treats diabetes (P<0.001 compared to other Groups). In addition, the treatment received by Group 7 was capable of reversing diabetes already present with efficacy. Therefore, these results demonstrate that a composition comprising a methylated first plasmid comprising a polynucleotide encoding an autoantigen or a donor antigen under the control of a promoter capable of promoting the polynucleotide encoding the autoantigen or the donor antigen, and a second plasmid comprising a polynucleotide encoding a pro-apoptotic protein under the control of a promoter capable of promoting the polynucleotide encoding a pro-apoptotic protein delays the onset, prevents and treats the immune-mediated inflammatory disorder caused by an autoimmune reaction to the autoantigen or the donor antigen.

EXAMPLE II

Prevenetion of Diabetes

According to the present invention, the onset of diabetes in a human patient is delayed, treated or prevented, for example, as follows. First, the patient is selected based on the presence of circulating anti-insulin and anti-GAD autoantibodies, or other criteria as will be understood by those with skill in the art with reference to this disclosure. Next; the patient is injected intradermally with 0.05 mg/Kg of body weight of a substance according to the present invention. Referring now to FIG. 12, there is shown a schematic depiction of a substance according to the present invention for a composition for preventing, delaying the onset of or treating one or more than one immune-mediated inflammatory disorder in an organism who is susceptible to developing the immune-mediated inflammatory disorder, who is developing the immune-mediated inflammatory disorder or who has the immune-mediated inflammatory disorder. As can be seen, the substance comprises a plasmid comprising a polynucleotide encoding SGAD55, SEQ ID NO: 1, and BAX, SEQ ID NO:2, both under the control of the SV40p promoter. Further, the plasmid comprises a plurality of CpG motifs, and at least some of the plurality of CpG motifs are methylated. Further, the plasmid comprises additional components as shown, and as disclosed above. The injection is repeated weekly while the level of circulating anti-insulin and anti-GAD autoantibodies is monitored. The treatment is ended when the level of circulating anti-insulin and anti-GAD autoantibodies, or the other criteria, has returned to a normal level.

Although the present invention has been discussed in considerable detail with reference to certain preferred embodiments, other embodiments are possible. Therefore, the scope of the appended claims should not be limited to the description of preferred embodiments contained in this disclosure.

The invention claimed is:

1. A composition for treating diabetes, comprising:
   a) an isolated first plasmid comprising a polynucleotide encoding a secreted glutamic acid decarboxylase (sGAD), but not a pro-apoptotic protein, under the control of a first promoter capable of promoting transcription of the polynucleotide encoding said sGAD; and
   b) an isolated second plasmid, which is separate and distinct from the first plasmid, the second plasmid comprising a polynucleotide encoding a BAX, but not an autoantigen or a donor antigen, under the control of a second promoter capable of promoting transcription of the polynucleotide encoding said BAX;
   where the first plasmid comprises a plurality of methylated CpG motifs; and
   wherein said composition, when administered to a mammalian subject, reduces a blood glucose level in the subject.

2. The composition of claim 1, where the second plasmid comprises a plurality of methylated CpG motifs.

3. The composition of claim 1, where the first plasmid and second plasmid are in a ratio of between 1/10 to 10/1.

4. The composition of claim 1, where said sGAD is human sGAD.

5. The composition of claim 1, where said sGAD comprises SEQ ID NO: 1.

6. The composition of claim 1, where the polynucleotide encoding said sGAD or BAX is selected from the group consisting of DNA and RNA.

7. The composition of claim 1, where said BAX is human BAX.

8. The composition of claim 1, where said BAX comprises SEQ ID NO: 2.

9. The composition of claim 1, where the methylated first plasmid is prepared by amplification in and isolation from a bacterial strain expressing SssI methylase.

10. The composition of claim 1, where the methylated first plasmid is resistant to digestion by the restriction enzyme HpaII.

11. The composition of claim 1, where the plurality of methylated CpG motifs are methylated by SssI methylase.

* * * * *

SEQUENCE LISTING

```
<160> NUMBER OF SEQ ID NOS: 3

<210> SEQ ID NO 1
<211> LENGTH: 1638
<212> TYPE: DNA
<213> ORGANISM: Artificial Sequence
<220> FEATURE:
<223> OTHER INFORMATION: secreted form of human GAD

<400> SEQUENCE: 1
atgtacagga tgcaactcct gtcttgcatt gcactaagtc ttgcacttgt cacaaacagt      60
gcacctactt acgcgtttct ccatgcaaca gacctgctgc cggcgtgtga tggagaaagg     120
cccactttgg cgtttctgca agatgttatg aacattttac ttcagtatgt ggtgaaaagt     180
ttcgatagat caaccaaagt gattgatttc cattatccta atgagcttct ccaagaatat     240
aattgggaat tggcagacca accacaaaat ttggaggaaa tttttgatgca ttgccaaaca     300 actctaaaat atgcaattaa aacagggcat cctagatact tcaatcaact ttctactggt     360
ttggatatgg ttggattagc agcagactgg ctgacatcaa cagcaaatac taacatgttc     420
```

```
acctatgaaa ttgctccagt atttgtgctt ttggaatatg tcacactaaa gaaaatgaga      480
gaaatcattg gctggccagg gggctctggc gatgggatat tttctcccgg tggcgccata      540
tctaacatgt atgccatgat gatcgcacgc tttaagatgt tcccagaagt caaggagaaa      600
ggaatggctg ctcttcccag gctcattgcc ttcacgtctg aacatagtca ttttctctc       660 aagaagggag ctgcagcctt agggattgga agagacagcg tgattctgat taaatgtgat      720
gagagaggga aaatgattcc atctgatctt gaaagaagga ttcttgaagc caaacagaaa      780
gggtttgttc ctttcctcgt gagtgccaca gctggaacca ccgtgtacgg agcatttgac      840
cccctcttag ctgtcgctga catttgcaaa aagtataaga tctggatgca tgtggatgca      900
gcttggggtg ggggattact gatgtcccga aaacacaagt ggaaactgag tggcgtggag      960
agggccaact ctgtgacgtg gaatccacac aagatgatgg gagtcccttt gcagtggtct     1020
gctctcctgg ttagagaaga gggattgatg cagaattgca ccaaatgca tgcctcctac      1080 ctctttcagc aagataaaca ttatgacctg tcctatgaca ctggagacaa ggccttacag     1140
tgcggacgcc acgttgatgt ttttaaacta tggctgatgt ggagggcaaa ggggactacc     1200
gggtttgaag cgcatgttga taaatgtttg gagttggcag agtatttata caacatcata     1260
aaaaaccgag aaggatatga gatggtgttt gatgggaagc tgaggacac aaatgtctgc      1320 ttctggtaca ttcctccaag cttgcgtact ctggaagaca atgaagagag aatgagtcgc     1380
ctctcgaagg tggctccagt gattaaagcc agaatgatgg agtatggaac cacaatggtc     1440
agctaccaac ccttgggaga caaggtcaat ttcttccgca tggtcatctc aaacccagcg     1500
gcaactcacc aagacattga cttcctgatt gaagaaatag aacgccttgg acaagattta     1560
taataacctt gctcaccaag ctgttccact tctctaggta gcgacctcga gcggccgctc     1620
gagggggggc ccggtacc                                                   1638

<210> SEQ ID NO 2
<211> LENGTH: 579
<212> TYPE: DNA
<213> ORGANISM: Homo sapiens

<400> SEQUENCE: 2
atggacgggt ccggggagca gcccagaggc ggggggccca ccagctctga gcagatcatg       60
aagacagggg cccttttgct tcagggtttc atccaggatc gagcagggcg aatggggggg      120
gaggcacccg agctggccct ggaccggtg cctcaggatg cgtccaccaa gaagctgagc       180
gagtgtctca gcgcatcgg ggacgaactg gacagtaaca tggagctgca gaggatgatt       240
gccgccgtgg acacagactc cccccgagag gtcttttcc gagtggcagc tgacatgttt       300
tctgacggca acttcaactg gggccgggtt gtcgcccttt tctactttgc cagcaaactg      360
gtgctcaagg cccctgtgca caaggtgccg gaactgatca gaaccatcat gggctggaca      420
ttggacttcc tccgggagcg gctgttgggc tggatccaag accagggtgg ttgggacggc      480
ctcctctcct actttgggac gcccacgtgg cagaccgtga ccatctttgt ggcgggagtg      540
ctcaccgcct cgctcaccat ctggaagaag atgggctga                             579

<210> SEQ ID NO 3
<211> LENGTH: 619
<212> TYPE: DNA
<213> ORGANISM: Encephalomyocarditis virus

<400> SEQUENCE: 3
tctagataat acgactcact ataggggcgaa ttccccctct ccctcccccc cccctaacgt       60
```

```
tactggccga agccgcttgg aataaggccg gtgtgcgttt gtctatatgt tattttccac    120
catattgccg tcttttggca atgtgagggc ccggaaacct ggccctgtct tcttgacgag    180
cattcctagg ggtctttccc ctctcgccaa aggaatgcaa ggtctgttga atgtcgtgaa    240
ggaagcagtt cctctggaag cttcttgaag acaaacaacg tctgtagcga ccctttgcag    300
gcagcggaac cccccacctg gcgacaggtg cctctgcggc caaaagccag gtgtataaga    360
tacacctgca aaggcggcac aaccccagtg ccacgttgtg agttggaata gttgtggaaa    420
gagtcaaatg gctctcctca agcgtattca acaaggggct gaaggatgcc cagaaggtac    480
cccattgtat gggatctgat ctggggcctc ggtgcacatg ctttacatgt gtttagtcga    540
ggttaaaaaa cgtctaggcc ccccaaccac ggggacgtgg tttccttg aaaaacacga    600 ttattatatt gcctctaga                                                619
```